United States Patent
Zechlin et al.

(10) Patent No.: US 10,836,713 B2
(45) Date of Patent: Nov. 17, 2020

(54) METHOD FOR PRODUCING ISOCYANATES IN THE GAS PHASE

(71) Applicant: Covestro Deutschland AG, Leverkusen (DE)

(72) Inventors: Joachim Zechlin, Neuss (DE); Thomas Stetten, Cologne (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/619,530

(22) PCT Filed: Jun. 6, 2018

(86) PCT No.: PCT/EP2018/064847
§ 371 (c)(1),
(2) Date: Dec. 5, 2019

(87) PCT Pub. No.: WO2018/224529
PCT Pub. Date: Dec. 13, 2018

(65) Prior Publication Data
US 2020/0190021 A1 Jun. 18, 2020

(30) Foreign Application Priority Data
Jun. 8, 2017 (EP) .................................... 17175067

(51) Int. Cl.
*C07C 263/10* (2006.01)
(52) U.S. Cl.
CPC ........ *C07C 263/10* (2013.01); *C07C 2601/16* (2017.05)
(58) Field of Classification Search
None
See application file for complete search history.

(56) References Cited

U.S. PATENT DOCUMENTS

| | | | |
|---|---|---|---|
| 4,847,408 A | 7/1989 | Frosch et al. | |
| 5,633,396 A | 5/1997 | Bischof et al. | |
| (Continued) | | | |

FOREIGN PATENT DOCUMENTS

| | | |
|---|---|---|
| EP | 2463273 A1 | 6/2012 |
| WO | 2013/029918 A1 | 3/2013 |

OTHER PUBLICATIONS

International Search Report, PCT/EP2018/064847, dated Aug. 20, 2018, Authorized officer: Wolfgang Fitz.

*Primary Examiner* — Amy C Bonaparte
(74) *Attorney, Agent, or Firm* — Donald R. Palladino (57) ABSTRACT

The invention relates to a method for producing isocyanates by phosgenating the corresponding primary amines in the gas phase, wherein the raw gaseous reaction product mixture is cooled and partially condensed by being brought into contact with at least one flow of a quenching liquid, and using a part of the condensed reaction product mixture as a component, optionally the only component, of the at least one flow of the quenching liquid after an additional cooling process. The quenching liquid used in total comprises, based on the total mass, organic solvents in a proportion of maximally 25% by mass, and the remainder of up to 100% by mass consists of at least the isocyanate to be produced. Furthermore, the reaction product mixture components which are not condensed under the influence of the quenching liquid are freed of isocyanate components in a scrubber column, and a scrubber liquid- and isocyanate-containing liquid flow is obtained with, based on the total mass, a content of organic solvents of 0.0% by mass up to 10% by mass, in particular 0.0% by mass up to 5.0% by mass.

15 Claims, 4 Drawing Sheets

(56) References Cited

U.S. PATENT DOCUMENTS

| | | |
|---|---|---|
| 6,803,482 B2 | 10/2004 | Jenne et al. |
| 6,838,578 B2 | 1/2005 | Leimkuhler et al. |
| 6,930,199 B2 | 8/2005 | Meyn et al. |
| 6,974,880 B2 | 12/2005 | Biskup et al. |
| 7,754,915 B2 | 7/2010 | Herold et al. |
| 2003/0069441 A1 | 4/2003 | Leimkuhler et al. |
| 2003/0230476 A1 | 12/2003 | Brady et al. |
| 2004/0068137 A1 | 4/2004 | Herold et al. |
| 2005/0070734 A1 | 3/2005 | Wolfert et al. |
| 2007/0043233 A1 | 2/2007 | Sanders et al. |
| 2008/0027242 A1 | 1/2008 | Knosche et al. |
| 2008/0146834 A1 | 6/2008 | Pohl et al. |
| 2008/0167490 A1 | 7/2008 | Pohl et al. |
| 2008/0200722 A1 | 8/2008 | Wolfert et al. |
| 2010/0154484 A1 | 6/2010 | Biskup et al. |
| 2010/0160673 A1 | 6/2010 | Bruns et al. |
| 2011/0257428 A1 | 10/2011 | Knoesche et al. |
| 2012/0004445 A1 | 1/2012 | Lehr et al. |
| 2012/0123152 A1 | 5/2012 | Bruns et al. |
| 2013/0060062 A1* | 3/2013 | Mattke ............ C07C 263/10 560/347 |
| 2015/0368190 A1 | 12/2015 | Steffens et al. |
| 2016/0152558 A1 | 6/2016 | Steffens et al. |

\* cited by examiner

METHOD FOR PRODUCING ISOCYANATES IN THE GAS PHASE

CROSS-REFERENCE TO RELATED APPLICATION

This application is a U.S. National Phase application under 35 U.S.C. § 371 of International Application No. PCT/EP2018/064847, filed Jun. 6, 2018, which claims priority to European Patent Application EP17175067.2, filed Jun. 8, 2017, which are each incorporated herein by reference.

FIELD

The invention relates to a process for preparing isocyanates by phosgenating the corresponding primary amines in the gas phase, in which the crude gaseous reaction product mixture is cooled down and partly condensed by contacting with at least one stream of a quench liquid, and using a portion of the condensed reaction product mixture, after further cooling, as a constituent, optionally the sole constituent, of the at least one stream of the quench liquid, where the total amount of quench liquid used, based on its total mass, comprises organic solvents in a proportion of at most 25% by mass, where the remainder to 100% by mass consists of at least the isocyanate to be prepared, where the fractions of the reaction product mixture not condensed under the influence of the quench liquid are also freed of isocyanate components in a scrubbing column, where a scrubbing liquid and isocyanate-comprising liquid stream with a proportion of organic solvents based on its total mass of 0.0% by mass to 10.0% by mass, especially of 0.0% by mass to 5.0% by mass, is obtained.

BACKGROUND

There have long been descriptions in the prior art of the preparation of isocyanates, especially diisocyanates, in the gas phase, which is utilized industrially, particularly for preparation of tolylene diisocyanate, xylylene diisocyanate, pentane 1,5-diisocyanate, hexamethylene 1,6-diisocyanate, isophorone diisocyanate and diisocyanatodicyclohexylmethane. In all processes, a gaseous crude product is obtained that comprises at least isocyanate, hydrogen chloride and any unconverted phosgene (phosgene is generally used in excess), and which has to be subjected to further workup in order to obtain the desired isocyanate in pure form.

Such a process is described, for example, in EP 0 289 840 B1. The diisocyanates formed in a tubular reactor are thermally unstable at the reaction temperatures of up to 500° C. Rapid cooling of the reaction gases after the phosgenation reaction to temperatures below 150° C. is therefore necessary to avoid the formation of unwanted by-products by the thermal breakdown of diisocyanate or by a further reaction. In EP 0 289 840 B1 or EP 0749 958 B1, for this purpose, the gaseous mixture that leaves the reaction space continuously and includes diisocyanate, phosgene and hydrogen chloride is introduced into an inert solvent, e.g. dichlorobenzene.

There are also known processes that use heat exchangers to cool down the reaction gases and/or expand the gases under reduced pressure (DE 101 58 160 A1).

It is preferable in the current prior art to bring about the cooling of the reaction gases by injecting liquids that are inert under the reaction conditions with very substantial condensation of the isocyanate formed. This is done in what is called a cooling or quenching zone. The aim is, during the cooling, to largely prevent further reaction in the liquid phase to give unwanted by-products (for example isocyanurates, biurets, allophanates, carbodiimides or ureas).

In the process according to WO 2005/123665 A1, attempts are made to reduce the dwell time between the end of the reaction and cooling zone by the presence of a region with reduced flow cross section between the reaction zone and the zone in which the termination of reaction is brought about. Suitable liquids to be injected include solvent, isocyanate or mixtures of solvent and isocyanate.

WO 2011/003532 A1 also discloses a process for rapid cooling of the gaseous reaction mixture by injecting a quench liquid into the gas mixture flowing continuously from the reaction zone into the downstream quench zone. Suitable quench liquids mentioned are solvent, isocyanate or solvent/isocyanate mixtures.

The injection of quench liquid by means of at least two spray nozzles disposed at the entrance to the quench zone is disclosed in EP 1 403 248 A1. Suitable quench liquids here are organic solvents or a mixture of different organic solvents that do not react with the diisocyanate formed. A solution of the diisocyanate formed in a suitable organic solvent can also be used, which reduces the amount of solvent used. In this case, the proportion by volume of the solvent in the quench liquid is from 40% to 90%, i.e. the proportion by volume of isocyanate is up to 60%. The diameter of the quench zone may be greater or smaller than the diameter of the reaction zone.

This system is optimized according to the teaching of EP 1 935 875 A1 in that, to stop the reaction, the reaction mixture is conducted out of the reaction space through a cooling section into which liquids are injected into two zones, such that the direct cooling in the cooling section is effected to obtain just one condensation mixture in two or more cooling zones connected in series. The diisocyanate produced is obtained here in a common condensation mixture. This mixture is preferably collected in a liquid collecting vessel arranged below the cooling section. This condensation mixture can be discharged to separate off the isocyanate prepared or, preferably after cooling, partly recycled to one or more cooling zones of the cooling section. The stream recycled in this way especially contains 30% to 90% by weight of solvent and 10% to 70% by weight of isocyanate. As well as the condensation mixture in the collecting vessel, a gas stream comprising at least hydrogen chloride, phosgene, optionally solvent, and the isocyanate prepared is obtained downstream of the cooling section. This gas stream is removed from the collecting vessel and sent to a scrubbing column, where it is largely freed of its isocyanate components. This scrubbing is preferably effected in countercurrent flow with solvent. The wash phase thus obtained, consisting of diisocyanate and predominantly of solvent, in a preferred embodiment, is used as quench liquid for the first cooling zone of the cooling section. In the downstream cooling zone(s), preference is given to using the condensation mixture from the collecting vessel (containing 10% to 70% by weight of isocyanate and 30% to 90% by weight of solvent) as quench liquid.

EP 1 935 876 A1 likewise mentions the use of various suitable quench liquid streams. Reference is also made to the use of the scrubbing liquid from the gas scrubbing of the vapor leaving the condensate collecting vessel downstream of the quench as quench liquid. Also mentioned is the possibility of using isocyanate as quench liquid (paragraph [0032]).

Multiple cooling zones in the quench stage are also referenced by EP 2 196 455 A1. This is the first reference to the integration of the cooling zones of multiple reactors with a quench stage. Here too, the option of using isocyanate as quench liquid is mentioned (paragraph [0055]).

Application WO 2007/014936 A2, Method for producing isocyanates (in the gas phase), describes a quench zone in which the gaseous crude product is cooled down rapidly by injecting a quench liquid. In this quench zone, the reaction mixture consisting essentially of the isocyanates, phosgene and hydrogen chloride is mixed vigorously with the liquid injected. The mixing is effected in such a way that the temperature of the reaction mixture is lowered proceeding from 200 to 570° C. down to 100 to 200° C., and the isocyanate present in the reaction mixture is transferred wholly or partly to the injected liquid droplets as a result of condensation, while the phosgene and the hydrogen chloride remain essentially completely in the gas phase. Possible quench liquids mentioned are solvent, isocyanate and solvent/isocyanate mixtures. The injection of a quench liquid is mentioned for cooling of the reaction mixture and selective dissolution of the diisocyanate formed in the solvent, with a first separation into a liquid phase and a gas phase comprising predominantly phosgene and hydrogen chloride as constituents. The two phases are then sent to an appropriate workup. There is no discussion of optimization options for this process step.

WO 2010/063665 A1 refers to a possible problem with the quench variants mentioned so far. If at least some of the quench liquid is withdrawn from the collecting vessel downstream of the quench, i.e. the liquid crude product mixture, it is possible that solids that can block the quench nozzles may be present. Various techniques, for example centrifuging, distilling off the liquid component intended for the quench or filtering, are described. In order to adjust the temperature of the selected quench stream for the stated problem, the stream can be cooled or heated up by means of a heat exchanger. This document discloses (page 12 lines 6 to 9, page 13 second paragraph) various sources for the quench medium: a substream 15 branched off from the phase separator 9 downstream of the quench 3 (which necessarily also contains isocyanate liquefied in the quench), fresh solvent 19, a portion of the liquid phase 13 obtained in the phase separator, and a substream of the biphasic product stream 7.

WO 2010/115908 A2 discloses a specific embodiment of the quench. In order to prevent further reactions of the reaction gas in or downstream of the quench stage, the quench nozzles and their arrangement are designed such that largely complete wetting of the wall is effected in the quench region. This affects the entire reaction mixture. Quench liquids proposed are solvents and mixtures with isocyanate or crude mixture from the phosgenation reaction, optionally after removal of particles. The proportion of isocyanate in the liquid with which the walls are wetted or in the quench medium may be in the range from 0 to 100 percent (page 11 lines 5 to 8).

EP 2 463 273 A1 discloses a process variant for isocyanate concentrations of greater than 70% by mass in the liquid bottom product leaving the quench zone. The stream leaving the quench zone in gaseous form is guided directly into a jacket-cooled condenser without passing through a scrubbing column. The remaining gas stream is sent directly to the phosgene recovery. In spite of the high temperature and high isocyanate concentration in the liquid bottom product from the quench zone, no statements are made as to residual isocyanate contents in the remaining gas stream. The condensate stream is combined with the condensate of the vapor stream, which results from expansion of the liquid bottom product from the quench zone, and recycled as quench liquid.

WO 2013/029918 A1 describes a process for preparing isocyanates by reacting the corresponding amines with phosgene, including in the gas phase. It is also the intention here that the process be performable at different loads on the gas phase plant without difficulty; more particularly, even in the case of running the plant in the part-load range, mixing and/or reaction is to be effected within the respectively optimized dwell time window, by increasing the ratio of phosgene to amine or adding one or more inert substances to the phosgene and/or amine stream. In this connection, the application also describes (page 9 last paragraph to page 12 first paragraph) various means of performing a quench of the gaseous crude product (quench with and without solvent, use of cooled product stream as quench medium, use of a condenser downstream of the quench). With regard to the fraction of the crude product leaving the quench in gaseous form, scrubbing thereof with a solvent is disclosed (page 12 third paragraph). The application does not disclose that this gas scrubbing can also be operated with only a low solvent content or even entirely without solvent. Since a gas phase process for preparing isocyanates in which the gaseous crude product stream passes through a quench cannot be operated economically without recycling of the proportion of the isocyanate uncondensed in the quench, it therefore also cannot be inferred from this application that the workup of an isocyanate prepared by such a gas phase reaction can indeed be conducted with a low solvent level or even without solvent. The various advantages of such a mode of operation, such as, in particular, the possibility of feeding the isocyanate-laden wash stream directly to the further workup of the crude isocyanate product liquefied in the quench, and the possibility of dispensing with a dedicated solvent column for recovering the solvent used, are therefore not suggested by this application.

WO 2014/122180 A1 concerns a process regime which makes it possible to completely dispense with recycling of the condensation mixture obtained in the quench zone into the quench. For this purpose, the gas phase obtained in the quench is partially condensed before being introduced into a scrubbing column, and the resulting condensate is used as additional quench liquid instead of recycled condensation product.

WO 2015/011070 A1 concerns the prevention of deposits in the region of the quench. What is taught is to keep the temperature of the wall of the reaction zone immediately above the quench zone at a value of at most 15% below the maximum temperature of the wall of the reaction zone reported in kelvin. Suitable quench liquids mentioned are solvent, isocyanate and mixtures of solvent and isocyanate.

Figure 1:
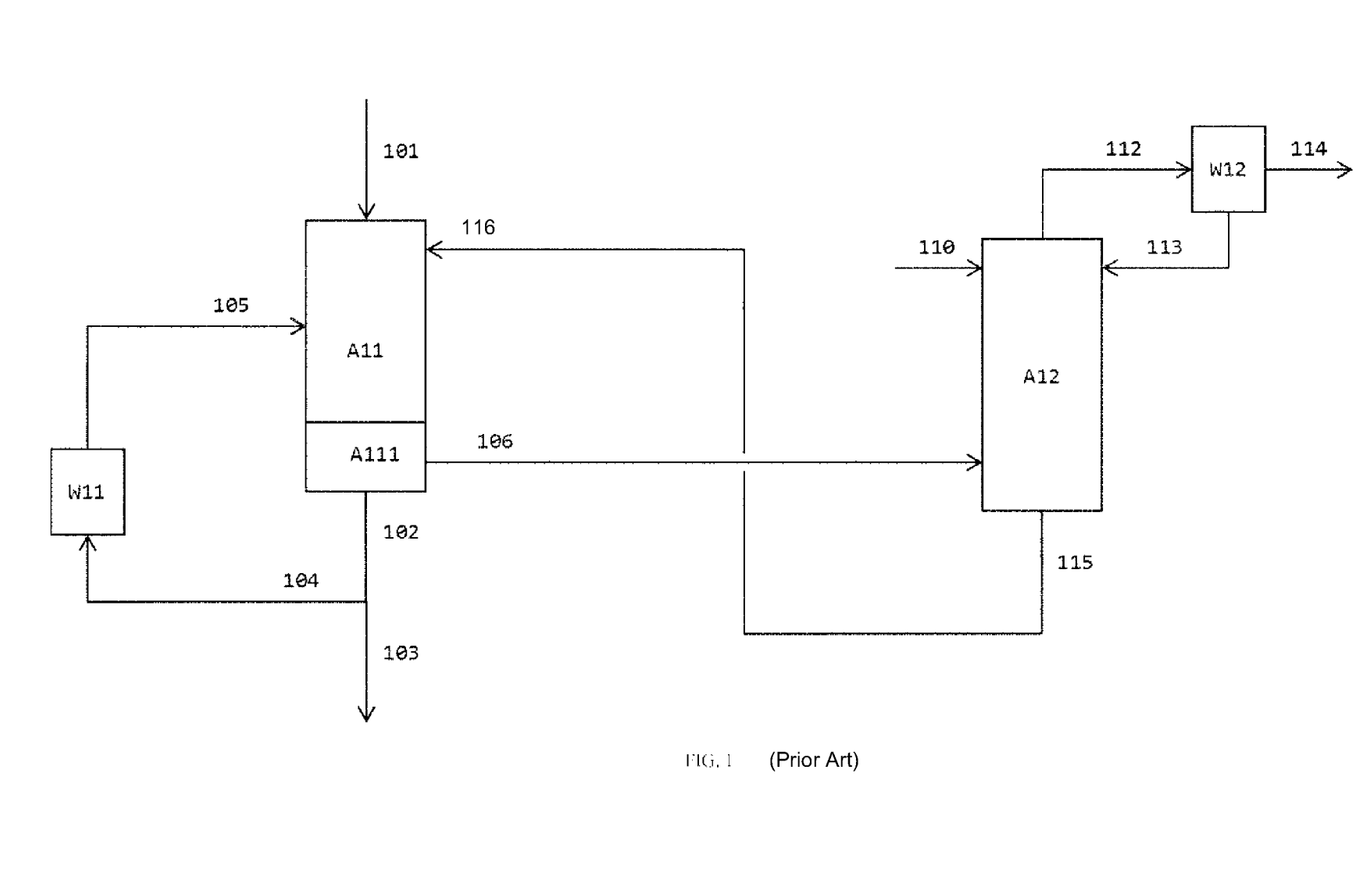
FIG. 1 illustrates a process flow of a two-stage quench of a crude product gas stream of the state of the art, whereby in the first stage of the two-stage quench a liquid bottoms effluent (115) of a scrubbing column (A12) is used as quench liquid, whereby said liquid bottoms effluent (115) contains mainly solvent.

In summary, it can be stated that, in the prior art, the injection of liquids that are inert under the reaction conditions into the crude product gas stream is the preferred variant for rapid cooling and condensation of the product. The at least two-stage quench in which a predominantly solvent-containing quench liquid is used in a first quench stage—viewed in flow direction of the product gas mixture, and a quench liquid consisting to a considerable degree of the isocyanate to be formed is used in a downstream second quench has been found here to be particularly advantageous. One possible embodiment of this method is elucidated hereinafter with reference to the first figure (FIG. 1):

The gaseous crude product (101), consisting primarily of isocyanate, hydrogen chloride and phosgene used in a superstoichiometric amount, is rapidly cooled in the quench (A11) by injecting quench liquid (105 and 116) in order to avoid unwanted further reactions. The liquid stream (102) that leaves the collecting container (A111) in the lower region of the quench and contains mainly isocyanate and quench liquid (especially 10% to 70% by weight of isocyanate and 30% to 90% by weight of solvent; cf. EP 1 935 875 A1, 25 paragraph [0042]), is guided partly to the product purification (103) and partly recycled to the quench (104) via the quench cooler (W11) as quench liquid.

The material flow (106) that leaves the quench in gaseous form, comprising mainly evaporated quench liquid, hydrogen chloride and phosgene, is sent to a scrubbing column (A12) to remove residual contents of isocyanate as far as possible from the vapor stream. The greater the content of isocyanates in the material flow (106) fed in, the higher the flow rate of scrubbing liquid stream (solvent) supplied at the top of the scrubbing column has to be, and the more separation plates are required for reliable retention. The vapors (112) from the scrubbing column pass through a condenser (vapor condenser W12). The scrubbing liquid stream is composed of the condensate (113) from the condenser (W12) and additional solvent (110). The virtually isocyanate-free vapor stream (114) contains mainly phosgene and hydrogen chloride. The liquid bottoms effluent (115) contains mainly solvent (in contents from 80 to 99.99% by weight; cf. EP 1 935 875 A1, paragraph [0042]) and is fed as quench liquid (116) to the quench.

Operational experience has shown that the operation of the quench in this way, although possible in principle and superior to many other process regimes, is not without disadvantages. In particular, contrary to any expectation, it has been observed that, particularly in the region of the first quench in flow direction of the product gas mixture, operated predominantly with solvent, deposits are formed over time, and these in the worst case can necessitate shutdown and cleaning of the reactor. Moreover, solids formed in or introduced into the reaction zone or quench zone and high boilers get into the quench cooler (W11) and the quench nozzles, and under some circumstances even into the scrubbing column (A12) and the condenser (W12), with the liquid quench product and can cause soiling anywhere therein. Furthermore, the dilution of the crude isocyanate material by virtue of the cooling of the gaseous reaction product mixture with a stream having a high solvent content has the fundamental disadvantage that the solvent supplied has to be removed again by thermal means in the course of further product workup. Amounts of energy which cannot be neglected are needed for that purpose. In addition, in the case of injection of a stream having a high solvent content into the quench zone, the evaporation of a portion of the solvent generates a vapor stream which contributes considerably to the total volume of the gas stream leaving the quench stage and in this way increases the expenditure associated with the removal of isocyanate entrained in this gas stream, for instance in that this results in greater dimensions of the apparatuses used. Moreover, there is the risk that the large amount of vapor will entrain any solid deposits present out of the reactor into the downstream separation of isocyanate from the gaseous stream obtained in the quench and will lead to blockages in apparatuses therein.

SUMMARY

Building on this prior art, there was therefore a need for further optimization of the quench of a gaseous crude isocyanate product. More particularly, it was desirable to improve the quench to the effect that deposits in the quench region are avoided or at least reduced, without significantly impairing the quality and processibility of the resultant condensation product. It was also desirable to minimize the content of solvent in the condensation product obtained in the quench because it is necessary to separate off the solvent present therein again in the workup. In particular, it was therefore also desirable to be able to configure the workup with maximum simplicity and hence in a particularly energy-efficient manner.

Taking account of the above, the present invention provides a process for preparing an isocyanate by phosgenating the corresponding primary amine in the gas phase, comprising the steps of:

(i) providing a gaseous stream of a primary amine;
(ii) providing a gaseous phosgene stream;
(iii) mixing the gaseous stream of the primary amine from step (i) and the gaseous phosgene stream from step (ii) to give a gaseous reaction mixture while maintaining a stoichiometric excess of phosgene relative to primary amino groups in a mixing zone and conducting the gaseous reaction mixture thus obtained through a reaction zone for reaction of the primary amine with phosgene to obtain a gaseous reaction product mixture;
(iv) cooling the gaseous reaction product mixture obtained after passage through the reaction zone from step (iii) by contacting with at least one stream of a quench liquid in a quench zone, where the total quench liquid used, based on its total mass, comprises organic solvents in a proportion of at most than 25% by mass, preferably at most 10% by mass, more preferably at most 5.0% by mass, most preferably 0.0% by mass, where the remainder to 100% by mass consists of at least the isocyanate to be prepared, to obtain a mixture of reaction product mixture and quench liquid;
(v) conducting the mixture of reaction product mixture and quench liquid obtained in step (iv) into a collecting zone for phase separation, where a liquid phase comprising isocyanate and a gaseous phase comprising hydrogen chloride, unconverted phosgene and unliquefied isocyanate are withdrawn from the collecting zone;
(vi) cooling a portion of the liquid phase comprising isocyanate withdrawn from the collecting zone in step (v), and using the cooled liquid phase of otherwise unchanged composition thus obtained in step (iv) as a constituent, optionally as the sole constituent, of the quench liquid;
(vii) working-up the portion of the liquid phase comprising isocyanate withdrawn from the collecting zone in step (v) that has not been cooled down in step (vi) and used in step (iv) to obtain the isocyanate (i.e. to obtain the isocyanate to be prepared in purified form, pure isocyanate);
(viii-1) optionally partly condensing the gaseous phase comprising hydrogen chloride, unconverted phosgene and unliquefied isocyanate which is obtained in step (v) by cooling to obtain a liquid stream comprising isocyanate and a gaseous stream comprising hydrogen chloride, phosgene and unliquefied isocyanate;
(viii-2) guiding either
when step (viii-1) is conducted, the gaseous stream comprising hydrogen chloride, phosgene and unliquefied isocyanate which is obtained in step (viii-1) or when step (viii-1) is not conducted, the gaseous phase comprising hydrogen chloride, unconverted phosgene and unliquefied isocyanate which is obtained in step (v)

into a scrubbing column in which isocyanate is scrubbed out with a scrubbing liquid to obtain a liquid stream comprising scrubbing liquid and isocyanate and a gaseous stream comprising hydrogen chloride and phosgene, and the gaseous stream comprising hydrogen chloride and phosgene obtained here is partly condensed in a condenser downstream of the scrubbing column (referred to henceforth as vapor condenser), where the scrubbing liquid used overall in step (viii-2) is composed of the condensate obtained in the vapor condenser and optionally additionally supplied scrubbing liquid, where the additionally supplied scrubbing liquid introduces organic solvent into the scrubbing column at most in such an amount that a proportion of organic solvents of 0.0% by mass to 10% by mass, preferably of 0.0% by mass to 5.0% by mass, is established in the liquid stream comprising scrubbing liquid and isocyanate which is obtained in the scrubbing column, based on the total mass thereof.

DETAILED DESCRIPTION

According to the invention, the "total amount of quench liquid used in step (iv), based on its total mass," has a proportion of organic solvents of "at most 25% by mass, preferably at most 10% by mass, more preferably at most 5.0% by mass, most preferably 0.0% by mass". If exactly one stream of quench liquid is used in step (iv) (i.e. if exclusively the liquid phase obtained after cooling in step (vi) is used as quench liquid), this stream must meet these requirements on maximum solvent content. If two or more streams of quench liquid from different sources with different composition are used in step (iv), the solvent content value averaged over all the streams of quench liquid used in step (iv) (i.e. the proportion based on the total mass of the quench liquid used overall) must meet these requirements (preferably, each individual stream of quench liquid used in step (iv) meets the aforementioned requirements on maximum solvent content and otherwise consists of at least the isocyanate to be prepared). "Organic solvents" (solvents for the purposes of the invention are always organic solvents) here are organic diluents which have no phosgene-reactive groups and in which the isocyanate to be prepared is soluble under standard conditions (20° C., 1013 mbar) and which are liquid under standard conditions (20° C., 1013 mbar) and are added to the process, but of course differ from these. The amount of such solvents added to the process is known; the solvent content in the total amount of quench liquid used in step (iv) can be readily ascertained by the person skilled in the art from this and from the boundary conditions that are likewise known (site of addition, temperatures and pressures, flow rates of the other feedstocks). The proportion of the total amount of quench liquid used that does not originate from such solvents consists at least of isocyanate to be prepared. Further constituents may especially be high-boiling secondary components present in the liquid phase obtained in step (vi). Entirely surprisingly, it has been found that the sole use of quench liquid with such a limited proportion of organic solvents in conjunction with the recycling of a portion of the liquid phase obtained in the collecting zone as quench liquid does not lead—as would have been expected on the basis of the low solvent content—to a deterioration in the product quality owing to increased by-product formation or to increased formation of deposits, and that the scrubbing column for recovering the isocyanate components that pass through the quench in gaseous form can be operated here with a low solvent level, which enables simplifications in the further workup and considerably reduces the energy consumption of the overall process.

This development was unforeseeable to the person skilled in the art since, owing to the extremely high reaction temperature in the gas phase, in the presence of only low solvent concentrations and hence high isocyanate concentrations in the quench liquid injected, owing to the thermal lability of the isocyanate, side reaction is actually to be expected. This is especially true in the first quench stage in flow direction of the reaction product gas mixture since the isocyanate injected here is being contacted with a very hot isocyanate-containing reaction gas.

There firstly follows a brief summary of various possible embodiments of the invention:

In a first embodiment of the invention, which can be combined with all other embodiments, step (iii) is conducted adiabatically, wherein composition and temperature of the gaseous stream of the primary amine in step (i) and of the phosgene stream in step (ii) are each chosen such that, in step (iii), a temperature in the range from 250° C. to 450° C., preferably in the range from 270° C. to 425° C., more preferably in the range from 280° C. to 420° C., is established in the mixing zone and in the reaction zone.

In a second embodiment of the invention, which can be combined with all other embodiments, the temperature of the at least one stream of quench liquid used in step (iv) is adjusted to a value in the range from 50° C. to 250° C., preferably from 100° C. to 200° C., more preferably 120° C. to 190° C.

In a third embodiment of the invention, which can be combined with all other embodiments, the mass flow rate of the quench liquid used overall in step (iv) is chosen such that it is 2 times to 60 times, preferably 10 times to 50 times, more preferably 20 times to 40 times, the mass flow rate of gaseous stream of the primary amine from step (i).

In a fourth embodiment of the invention, which can be combined with all other embodiments, the contacting of the gaseous reaction product mixture with the quench liquid in step (iv) is effected by injecting the quench liquid into the gaseous reaction product mixture.

In a fifth embodiment of the invention, which is a particular configuration of the fourth embodiment, the injection of the quench liquid into the reaction product mixture is effected in one stage.

In a sixth embodiment of the invention, the scrubbing column is supplied not only with the condensate obtained in the vapor condenser but additionally with further scrubbing liquid, where this additionally supplied scrubbing liquid is a solvent stream containing exclusively an organic solvent selected from the group consisting of aliphatic hydrocarbons [preferably decahydronaphthalene], aromatic hydrocarbons having no halogen substitution [preferably toluene or xylene, especially toluene], aromatic hydrocarbons having halogen substitution [preferably chlorobenzene, para-dichlorobenzene, ortho-dichlorobenzene, chlorotoluene or chloronaphthalene, especially ortho-dichlorobenzene] and mixtures of the aforementioned solvents.

In a seventh embodiment of the invention, which is a particular configuration of the sixth embodiment, the mass flow rate of the solvent stream used as additional scrubbing liquid is adjusted such that it is in the range from 20% to 100%, preferably in the range from 50% to 100%, of the mass flow rate of the gaseous stream of the primary amine from step (i).

In an eighth embodiment of the invention, the liquid stream comprising scrubbing liquid and isocyanate which is obtained in the scrubbing column is sent to the workup in step (vii) (i.e. directly, without recycling into the quench zone from step (iv)).

In a ninth embodiment of the invention, which can be combined with all embodiments comprising step (viii-1) (except for the eleventh embodiment defined further down), the quench liquid used in step (iv), in addition to the cooled liquid phase of otherwise unchanged composition that has been obtained in step (vi), comprises the liquid stream comprising isocyanate that has been obtained in step (viii-1).

In a tenth embodiment of the invention, which can be combined with all embodiments (except for the eleventh embodiment defined further down), the quench liquid used in step (iv), in addition to the cooled liquid phase of otherwise unchanged composition that has been obtained in step (vi), comprises the liquid stream comprising scrubbing liquid and isocyanate that has been obtained in step (viii-2).

In an eleventh embodiment of the invention, which is an alternative to the ninth and tenth embodiments, the quench liquid used in step (iv), aside from the cooled liquid phase of otherwise unchanged composition that has been obtained in step (vi), does not comprise any further constituents.

In a twelfth embodiment of the invention, which can be combined with all other embodiments, the isocyanate is obtained in step (vii) by supplying the liquid phase comprising isocyanate to a distillative purification without an intermediate solvent column (i.e. a distillation column for removing solvent).

In a thirteenth embodiment of the invention, which is a particular configuration of the twelfth embodiment, the distillative purification is performed in a single distillation column which is especially configured as a dividing wall column.

In a fourteenth embodiment of the invention, which can be combined with all other embodiments, every individual stream of quench liquid used in step (iv), based on its total mass, comprises organic solvents in a proportion of at most 25% by mass, preferably at most 10% by mass, more preferably at most 5% by mass, most preferably 0.0% by mass.

In a fifteenth embodiment of the invention, which can be combined with all other embodiments, the primary amine is selected from the group consisting of tolylenediamine, diphenylmethanediamine, xylylenediamine, pentane-1,5-diamine, hexamethylene-1,6-diamine, isophoronediamine, diaminodicyclohexylmethane and mixtures of the aforementioned compounds, where tolylenediamine (TDA) is especially preferred.

In a sixteenth embodiment of the invention, which can be combined with all embodiments that do not entirely dispense with the use of organic solvents, the same organic solvent is used in all steps in which an organic solvent is used and is especially selected from the group consisting of aliphatic hydrocarbons [preferably decahydronaphthalene], aromatic hydrocarbons having no halogen substitution [preferably toluene or xylene, especially toluene], aromatic hydrocarbons having halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents.

In a seventeenth embodiment of the invention, which is a particular embodiment of the sixteenth embodiment, the organic solvent used is ortho-dichlorobenzene, especially in conjunction with TDA as the primary amine to be phosgenated.

The embodiments briefly outlined above and further possible configurations of the invention are elucidated in detail hereinafter. Various embodiments are combinable with one another as desired unless the opposite is clearly apparent to the person skilled in the art from the context.

In step (i), a stream of a primary amine in gaseous form is provided.

Suitable primary amines for the performance of this step are those which can be evaporated without decomposition, especially tolylenediamine (TDA hereinafter, especially meta-TDA), diphenylmethanediamine (often also called methylenediphenyldiamine, MDA hereinafter), xylylenediamine (XDA, especially meta-XDA), pentane-1,5-diamine (PDA hereinafter), hexamethylene-1,6-diamine (HDA hereinafter), isophoronediamine (IDPA hereinafter) and diaminodicyclohexylmethane (H12-MDA hereinafter). If the amines mentioned can be present in different isomeric forms without specification thereof, all isomer distributions are included. In principle, it is also possible to convert mixtures of the aforementioned amines, although this is generally not preferred.

Particular preference is given to TDA. Typically, TDA which is used with preference comprises 78.0% by mass to 82.0% by mass of 2,4-TDA and 18.0% by mass to 22.0% by mass of 2,6-TDA, based on the total mass of the 2,4- and 2,6-TDA isomers. Based on the total mass of the TDA, the 2,4- and 2,6-TDA isomers preferably account for a sum total of 95.0% by mass to 100% by mass, more preferably of 98.0% by mass to 100% by mass. Preferably, the content of TDA isomers having $NH_2$ groups in ortho positions to one another in the TDA used is less than 0.2% by mass, based on the total mass of the TDA used. Processes for providing TDA with the requirements mentioned are known to the person skilled in the art.

Methods of providing a gaseous amine stream for the performance of step (i) are known in principle to the person skilled in the art. Preferred embodiments are outlined hereinafter.

The amine can be converted to the gas phase in all evaporation apparatuses known from the prior art, especially in a falling-film evaporator. Preference is given to using those evaporation apparatuses in which a small volume of working contents is guided over a falling-film evaporator with a high circulation power.

In a preferred embodiment of the process of the invention, evaporation apparatuses in which a small volume of working contents is circulated through at least one micro heat exchanger or micro evaporator are used. The use of corresponding heat exchangers for the evaporation of amines is disclosed, for example, in EP 1 754 698 A2. Preference is given to using the apparatuses disclosed in paragraphs [0007] to [0008] and [0017] to [0039] of EP 1 754 698 A2 in the process of the invention.

For minimization of thermal stress on the amine, irrespective of the exact configuration of the evaporation apparatus, it is preferable to assist the evaporation operation by feeding in an inert gas such as $N_2$, He, Ar or the vapors of an inert solvent, preferably selected from the group consisting of aliphatic hydrocarbons [preferably decahydronaphthalene], aromatic hydrocarbons without halogen substitution [preferably toluene or xylene, especially toluene], aromatic hydrocarbons with halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents. If the amine is diluted in this way, preference is given to the use of an inert gas selected from the group consisting of $N_2$, He, Ar and mixtures thereof as diluent, dispensing with the use of vapors of an inert solvent.

In addition, the evaporation—and if required superheating—of the starting amine (especially to a temperature in the range from 200° C. to 430° C., preferably 250° C. to 420° C., more preferably 250° C. to 400° C.) is preferably effected in multiple stages in order to avoid unevaporated droplets in the gaseous amine stream. Especially preferred are multistage evaporation and superheating steps in which droplet separators are installed between the evaporation and superheating systems and/or the evaporation apparatuses also have the function of a droplet separator. Suitable droplet separators are known to those skilled in the art. After leaving the last superheater in flow direction, the gaseous amine preheated to its target temperature is sent to the mixing and reaction in step (iii) with an average dwell time of preferably 0.01 s to 60 s, even more preferably of 0.01 s to 30 s, especially preferably 0.01 s to 15 s. Irrespective of the configuration of the supply of the amine in detail, the risk of new droplet formation is preferably countered by means of technical measures, for example sufficient insulation for avoidance of radiative heat losses.

In step (ii), a gaseous phosgene stream is provided.

In the process of the invention, phosgene is used in excess relative to the amino groups to be converted. Preference is given to establishing a molar ratio of phosgene to amine groups of 1.1:1 to 20:1, more preferably 1.2:1 to 5.0:1. As described above for the amine, the phosgene is preferably also heated to a temperature in the range from 200° C. to 430° C., preferably 250° C. to 420° C., more preferably 250° C. to 400° C., and supplied to the mixing and reaction in step (iii) optionally diluted with an inert gas such as $N_2$, He, Ar or with the vapors of an inert solvent, preferably selected from the group consisting of aliphatic hydrocarbons [preferably decahydronaphthalene], aromatic hydrocarbons without halogen substitution [preferably toluene or xylene, especially toluene], aromatic hydrocarbons with halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents. If the phosgene is diluted, preference is given to the use of an inert gas selected from the group consisting of $N_2$, He, Ar and mixtures thereof as diluent, dispensing with the use of vapors of an inert solvent.

In step (iii), the amine and phosgene coreactants are mixed and reacted.

The separately heated amine and phosgene coreactants are preferably supplied via a nozzle arrangement to the mixing and conversion in step (iii). The nozzle arrangement for introduction of the amine and phosgene reactant gas streams may be configured in various ways known to the person skilled in the art; examples can be found, for example, in EP 2 199 277 B1, paragraphs [0017] to [0019], EP 1 449 826 B1, paragraphs [0011] to [0012], EP 1 362 847 B1, paragraphs [0011] to [0012], EP 1 526 129 B1, paragraphs [0009] to [0011] and EP 1 555 258 B1, paragraphs [0008] to [0011].

As well as the option already mentioned of diluting the gaseous stream of the primary amine and the gaseous phosgene stream, it is also possible to run a separate diluent gas stream (an inert gas such as $N_2$, He, Ar or the vapors of an inert solvent, preferably selected from the group consisting of aliphatic hydrocarbons [preferably decahydronaphthalene], aromatic hydrocarbons without halogen substitution [preferably toluene or xylene, especially toluene], aromatic hydrocarbons with halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents) directly into the mixing in step (iii). In this case, this diluent gas stream is preferably heated to a temperature in the range from 100° C. to 500° C., preferably 150° C. to 450° C., more preferably 150° C. to 400° C. If the mixing zone from step (iii) is supplied with such a diluent gas stream, preference is given to the use of an inert gas selected from the group consisting of $N_2$, He, Ar and mixtures thereof as diluent gas, dispensing with the use of vapors of an inert solvent.

The conversion in the reaction zone is preferably adiabatic. Adiabatic conversion means that controlled removal of the heat of reaction formed by a heat carrier medium is dispensed with. Therefore, the reaction enthalpy—apart from unavoidable heat losses—is reflected quantitatively in the temperature differential of product gas stream and reactant gas stream. More particularly, the invention also relates to a process in which step (iii) is conducted adiabatically and wherein composition and temperature of the gaseous stream of the primary amine in step (i) and the phosgene stream in step (ii) are each chosen such that, in step (iii), a temperature in the range from 250° C. to 450° C., preferably in the range from 270° C. to 425° C., more preferably in the range from 280° C. to 420° C., is established in the mixing zone and in the reaction zone. This means that the temperature at any point in the mixing zone and the reaction zone is within this range.

Mixing zone and reaction zone are disposed here preferably in a common technical apparatus for performance of chemical reactions, the reactor. In this arrangement, mixing zone and reaction zone generally have a fluid transition without the possibility of—as in the case of use of a separate mixing apparatus, which is also possible in principle—strict delimitation between the two. The reaction zone after mixing of the reactants serves to provide delay time in order to assure maximum conversion.

The reactor preferably has a round (especially circular symmetrical) cross section in the region of the mixing zone and in the region of the reaction zone. It is possible here for the entire reactor to be cylindrical. However, it is also possible that the cross section changes, as described, for example, in EP 1275639 B1, paragraph [0009], EP 1 275 640 A1, paragraph [0014], EP 1 403 248 B1, paragraphs [0014] to [0015], EP 193 5876 A1, paragraphs [0012] to [0016], and EP 2 196 455 B1, paragraphs [0015] to [0026] and [0027] to [0030]. Further details of the construction of suitable phosgenation reactors are known to those skilled in the art.

In the reaction zone, amine and phosgene are converted rapidly to the corresponding isocyanate, preferably adiabatically as described. The reaction is preferably conducted such that the amine is converted fully before entry into the quench zone described in detail further down. In a preferred embodiment of the process of the invention, the throughput capacity of the reactor used under reaction conditions is >1.0 t of amine/h, preferably 2.0 to 50 t of amine/h, more preferably 5.0 to 15 t of amine/h. These values are more preferably applicable to tolylenediamine, 1,6-diaminohexane and isophoronediamine "Throughput capacity" is understood to mean that the stated throughput capacity of amine per hour can be converted in the reactor.

Preferably, the reactant and product gases flow through the reactor without significant backmixing. This is ensured by a pressure gradient across the mixing zone and reaction zone, preferably across the mixing zone and reaction zone and the downstream quench zone. Preferably, the pressure gradient exists between the start of the mixing zone on the one hand and the exit from the quench zone on the other hand. Preferably, the absolute pressure at the start of the mixing zone is 200 mbar to 3000 mbar and that beyond the quench zone is 150 mbar to 2500 mbar. All that is essential here, however, is the maintenance of a pressure differential across the reaction zone, preferably across the reaction zone and the quench zone, preferably at least 40 mbar for assurance of the directed flow mentioned and good mixing of the reactants.

In step (iv), the isocyanate formed is rapidly cooled and largely liquefied ("quench").

What is meant by the requirement of the invention that "the total amount of quench liquid used, based on its total mass, has a proportion of organic solvents of at most 25% by mass, preferably at most 10% by mass, more preferably at most 5.0% by mass, most preferably 0.0% by mass" is that, in the context of the present invention, the use of quench liquid with a high solvent content (especially quench liquid with 30% to 90% by mass of solvent from the bottom product from the cooling section and/or even 80% to 99.99% by mass of solvent from the gas scrubbing; cf. EP 1 935 875 A1, paragraph [0042]) which is customary in the art is not employed. If the quench liquid used in step (iv) contains an organic solvent, it is preferably selected from the group consisting of aliphatic hydrocarbons [preferably decahydronaphthalene], aromatic hydrocarbons having no halogen substitution [preferably toluene or xylene, especially toluene], aromatic hydrocarbons having halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents.

After the phosgenation reaction in the reaction zone, the gaseous reaction product mixture comprising at least isocyanate to be prepared, hydrogen chloride and unconverted phosgene (since it is used superstoichiometrically) is guided into the quench zone, where the isocyanate formed is cooled down and hence (largely) condensed by contacting with, i.e. especially by injecting, quench liquid. Options for the construction and operation of a quench zone are known in principle from the prior art. If the demands of the invention with regard to the composition of the quench liquid are complied with, it is possible to use the apparatuses and methods from the prior art. Possible configurations of the quench zone are disclosed, for example, in EP 1 403 248 A1 and EP 1 935 875 A1. Compliance with the demands of the invention with regard to the composition of the quench liquid means that the total amount of quench liquid used in the overall quench step (iv) contains 0.0% by mass to 25.0% by mass of organic solvents, preferably 0.0% by mass to 10.0% by mass of organic solvents, more preferably 0.0% by mass to 5.0% by mass of organic solvents, based in each case on the total mass of the quench liquid used overall. Very exceptionally preferably, the quench liquid used overall does not comprise any organic solvent and consists—aside from impurities (for example, high-boiling secondary components in the liquid phase from step (vi)), which may be present in proportions of in particular up to 5.0% by mass, based on the total mass of the quench liquid used overall—of the isocyanate to be prepared. If multiple streams of quench liquid are used, the aforementioned composition ranges are applicable at least to the proportion by mass of organic solvents averaged over all streams of quench liquid used, but preferably to each individual stream of quench liquid.

If barely any solvent is introduced into the gas phase reaction, the mass flow rate of the gas phase obtained in step (v) is additionally also reduced, which leads to a simplification of the downstream workup steps, as elucidated in detail further down.

In a preferred embodiment, step (iv) is configured such that the quench liquid is injected into the reaction product mixture at just one position in the quench zone (one-stage quench). What is meant here by "at just one position" is a single position in the longitudinal direction of the reactor in a quench zone in an upright reactor having a round (especially circular symmetrical) cross section. It is quite possible here for the quench liquid to be distributed with the aid of multiple nozzles over the cross section of the quench zone. However, this is accomplished at the same position in the longitudinal direction of the reactor, by contrast with the procedure shown in FIG. 1 with supply of quench liquid at two different positions (see 116 and 105) in the longitudinal direction of the reactor.

The temperature of the quench liquid used in step (iv) is preferably chosen such that it is firstly high enough to cleave the carbamoyl chloride corresponding to the isocyanate to isocyanate and hydrogen chloride. (It is in no way certain whether the carbamoyl chloride intermediate known from the liquid phase phosgenation will also be formed in the gas phase phosgenation. Since, however, it is independently conceivable that liquefied isocyanate reacts partly with the hydrogen chloride gas present in the quench to give the carbamoyl chloride, the temperature of the quench liquid should be high enough to suppress this reaction.) On the other hand, isocyanate and any solvent additionally used as diluent in the gaseous amine stream and/or gaseous phosgene stream should very substantially condense or very substantially dissolve in the solvent, while excess phosgene, hydrogen chloride and any inert gas used additionally as diluent pass through the quench zone very substantially uncondensed and undissolved, such that the temperature of the quench liquid chosen must not become too high either. Of particularly good suitability for selectively obtaining the isocyanate from the gaseous reaction mixture are quench liquids kept especially at a temperature of 50° C. to 250° C., preferably 100° C. to 200° C., more preferably 120° C. to 190° C. (if multiple streams of quench liquid are used, the temperature of each stream of quench liquid is kept within this range). The mass flow rate of quench liquid used overall in step (iv) is preferably chosen here such that it is 2 times to 60 times, more preferably 10 times to 50 times, most preferably 20 times to 40 times, the mass flow rate of gaseous stream of the primary amine from step (i).

At a given temperature, pressure and composition, it is easy for the person skilled in the art on the basis of the physical data to predict what proportion by mass of the isocyanate will condense in the quench and what proportion will run through it uncondensed. It is likewise easy to predict what proportion by mass of the excess phosgene, hydrogen chloride, any solvent and any inert gas used as diluent will run through the quench uncondensed and what proportion will dissolve in the quench liquid. The mixture of reaction product mixture and quench liquid thus obtained in the quench zone therefore contains gaseous components and liquid components, i.e. is biphasic.

Mixing zone, reaction zone and quench zone are preferably disposed in a common apparatus, the reactor. Especially preferably, the reactor has a round (especially circular symmetrical) cross section in the region of the mixing zone, reaction zone and quench zone and is either cylindrical in shape or has—as described above—sections of different cross section, such that the reactor consists of cylinders of different diameter in the region of the mixing zone, reaction zone and quench zone, connected via conical transition pieces. The reactor here is preferably upright, and the amine and phosgene reactant gas streams (and the intermediates and end products formed therefrom) preferably pass through the reactor from the top downward. In that case, mixing zone, reaction zone and quench zone are arranged in that sequence from the top downward in the reactor. Preferably, the collecting zone outlined in detail hereinafter is also part of the reactor and, in the case of an upright arrangement thereof, is especially disposed below the quench zone. The collecting zone also preferably has a round (especially circular symmetrical) cross section; but other configurations are conceivable.

In step (v), the mixture of reaction product mixture and quench liquid obtained in step (iv) is guided into a collecting zone for phase separation.

In the above-detailed preferred embodiment of the common arrangement of mixing zone, reaction zone, quench zone and collecting zone from the top downward in that sequence in an upright reactor, the mixture of reaction product mixture and quench liquid obtained in step (iv) flows under gravity (i.e. "automatically") into the collecting zone. In another arrangement of the collecting zone, it may be necessary under some circumstances to pump the mixture of reaction product mixture and quench liquid into the collecting zone.

In the collecting zone, a separation of the mixture of reaction product mixture and quench liquid obtained in step (iv) into a liquid phase comprising isocyanate and optionally solvent and a gaseous phase comprising (at least) hydrogen chloride, unconverted phosgene and unliquefied isocyanate and—if present—evaporated solvent takes place. The liquid phase and gaseous phase are withdrawn continuously from the collecting zone.

In step (vi), a portion of the liquid phase withdrawn from the collecting zone in step (v) is cooled and recycled.

The cooling of a portion of the liquid phase withdrawn from the collecting zone is effected indirectly, i.e. without direct (physical) contact of the liquid phase withdrawn from the collecting zone with a liquid cooling medium. A heat exchanger is especially suitable for this purpose. The cooling in step (vi) is preferably effected to a temperature in the range from 30° C. to 245° C., preferably 80° C. to 195° C., more preferably 100° C. to 195° C., most preferably 100° C. to 185° C. Since this recycled liquid phase does not undergo any further treatment apart from the cooling, i.e. any further change, its composition in this embodiment corresponds to that of the liquid phase in the collecting zone.

Furthermore, the efficiency of the cooling of liquid phase withdrawn from the collecting zone by an external heat exchanger by the process of the invention can be increased considerably since the heat capacity of liquid phase is comparatively high owing to its low solvent content. Moreover, when the process of the invention is used, the efficiency of the external heat exchanger is additionally increased since the isocyanate now having only low solvent dilution, if any, owing to the better dissolution properties for residue components, is able to effectively protect the surfaces of the heat exchanger from deposits.

In one embodiment of the invention, the liquid phase present in the collecting zone, even before it has been withdrawn, can be cooled by recycling of a condensate from the residue workup—described in detail hereinafter—that consists almost entirely or completely of the isocyanate to be prepared (especially to an extent of 95% by mass to 100% by mass, based on the total mass of the condensate). This recycling firstly enables additional cooling of the liquid phase obtained in the collecting zone with reduction of the amount of isocyanate evaporated (i.e. with reduction of the gas phase formed step (v) and withdrawn from the collecting zone); secondly, the residue concentration in the bottom of the reactor can be kept low by dilution. The cooling effect is accompanied by heating of the condensate from the residue workup, which leads to a saving of energy since this material would otherwise have to be heated up again in the isocyanate distillation stage.

In further embodiments, sufficiently cooled isocyanate streams from any process steps can be recycled into the collecting zone in order to lead to cooling and dilution therein.

Preferably 50% to 96%, more preferably 60% to 94%, most preferably 70% to 92%, of the liquid phase withdrawn from the collecting zone in step (v) is recycled into step (vi) as quench liquid, while the remainder (called isocyanate raw material) is sent to a workup to obtain the isocyanate in purified form (pure isocyanate). The process of the invention, in particularly preferred embodiments, enables the provision of an isocyanate raw material having a content of organic solvents of at most 20% by mass, preferably at most 8.0% by mass, more preferably at most 4.0% by mass, even more preferably 0.0% by mass, based on the total mass of the isocyanate raw material.

In step (vii), the residual liquid phase not recycled as quench liquid from the collecting zone (isocyanate raw material) is worked up to obtain (isolate) the isocyanate in purified form (pure isocyanate).

This workup is preferably effected by distillation. Depending on the solvent content of the liquid phase obtained in the collecting zone, the workup can be effected in one or more stages.

If the liquid phase comprising isocyanate which is withdrawn from the collecting zone in step (v) contains substantial proportions of solvent (i.e. when the solvent content is more within the upper region of the range permissible in accordance with the invention), it may be advantageous to first free this liquid phase of the majority of the solvent in a first distillation step (vii-1) in what is called a solvent column, followed by, in at least one further distillation step (vii-2), a fine purification of isocyanate. The workup can be conducted as known from the prior art, especially as described in EP 1 371 633 A1. It is likewise possible for the distillation step (vii-1) to be preceded by a separate removal of dissolved phosgene and dissolved hydrogen chloride which is known from the prior art (step (vii-0)).

In principle, it is also possible to dispense with the aforementioned first distillation step (vii-1); the isocyanate raw material is then sent to the fine purification without intermediate solvent column(s). This is advantageous especially when the liquid phase comprising isocyanate that has been withdrawn from the collecting zone in step (v) contains small proportions at most of solvent (i.e. when the solvent content is more within the lower region of the range permissible in accordance with the invention). When the first distillation step is dispensed with, the liquid phase obtained in the collecting zone, to the extent that it is not recycled into the quench (step (iv)), is fed directly—or after at most a separate removal of dissolved phosgene and dissolved hydrogen chloride known per se from the prior art—to a distillation to obtain pure isocyanate. This distillation is preferably effected in a single distillation column which may especially be configured as a dividing wall column. As well as the obvious apparatus simplification, in this embodiment, the energy efficiency of the process is increased to a considerable degree by dispensing with the solvent evaporation.

Irrespective of the exact configuration of the distillative workup in step (vii), at least one distillation bottom stream is also obtained as well as the pure isocyanate obtained (as distillate stream) (for example the distillate bottom stream from the dividing wall column used in step (vii-2) in a preferred embodiment of the invention). This distillation bottom stream contains what is called the distillation residue and proportions of isocyanate to be prepared.

The distillation residue contains compounds that do not evaporate under the pressure and temperature conditions chosen for the distillation or that do not evaporate without decomposition at all. The compounds in the distillation residue that are evaporable with difficulty, if at all—if they are not impurities from the primary amine used that run through the phosgenation process unchanged—are phosgenation products of high molecular weight, the structure of which is still not exactly known. For instance, they may be compounds that can be derived (in a formal sense) from polymerization products of the amine used by replacement of the unpolymerized amine groups by isocyanate groups. Phosgenation products of higher molecular weight may also partly form (by further reaction) in step (vii).

The distillation bottom stream containing the distillation residue is preferably likewise worked up (step vii-3)), wherein this workup comprises the following steps:
a) optionally preconcentrating the distillation bottom stream in an evaporator by partially evaporating the isocyanate to be prepared which is present in the distillation bottom stream to obtain a pre-concentrated liquid stream depleted of isocyanate to be prepared;
b) drying of the distillation bottom stream or the preconcentrated liquid stream depleted of isocyanate to be prepared which has been obtained in step a) in a drying apparatus at a temperature in the range from 150° C. to 500° C., preferably in the range from 185° C. to 300° C., more preferably in the range from 200° C. to 270° C., and at a pressure in the range from 10 $\text{mbar}_{(abs.)}$ to 250 $\text{mbar}_{(abs.)}$, preferably in the range from 20 $\text{mbar}_{(abs.)}$ to 200 $\text{mbar}_{(abs.)}$, more preferably in the range from 30 $\text{mbar}_{(abs.)}$ to 100 $\text{mbar}_{(abs.)}$ is conducted, with evaporation and recovery of isocyanate to be prepared to form a solid process product.

This optional preconcentration by partial evaporation in step a) can in principle be effected in any evaporators known to those skilled in the art. More preferably, step a) is conducted in an evaporator selected from the group consisting of thin-film evaporators, climbing-film evaporators, falling-film evaporators, long tube evaporators, helical tube evaporators, forced circulation flash evaporators and a combination of these apparatuses. Particular preference is given here to falling-film evaporators. It is also possible to connect multiple evaporators in series. The preconcentration in step a) is preferably effected at a temperature in the range from 120° C. to 180° C. and at a pressure in the range from 20 $\text{mbar}_{(abs.)}$ to 60 $\text{mbar}_{(abs.)}$, more preferably at a temperature in the range from 130° C. to 175° C. and at a pressure in the range from 25 $\text{mbar}_{(abs.)}$ to 45 $\text{mbar}_{(abs.)}$. Step a) can be conducted continuously or batchwise. The continuous process regime is preferred.

In step b), the preconcentrated liquid stream that has been depleted of isocyanate to be prepared and is obtained in step a) or—when step a) is dispensed with—the distillation bottom stream is dried. Drying apparatuses suitable for step b) are preferably selected from the group consisting of heated, product-agitating vacuum driers with a horizontal shaft (preferably kneader-driers, paddle driers, shovel driers; wherein each of the driers mentioned may have exactly one shaft or multiple shafts, especially two shafts), rotary tubes, disk driers, belt driers and pelletizing screws. In the drying, the isocyanate to be prepared is evaporated and recovered. What remains is a solid material consisting virtually exclusively of distillation residue and still containing the isocyanate to be prepared in traces at most. The solid is preferably discharged continuously from the drying apparatus.

The isocyanate evaporated in step a) or in steps a) and b) is condensed. In the case of performance of steps a) and b), the condensates obtained are preferably combined. The proportion of isocyanate to be prepared which is recovered in this way is preferably combined partly to completely, preferably completely, with the pure isocyanate or recycled elsewhere in the process. It is possible, for example, to recycle the proportion of the isocyanate to be prepared that is obtained in step (vii-3) into step (vii-2), especially into the feed or into the distillation bottom stream of the distillation column used therein (in the case of multiple distillation columns connected in series preferably into the feed or into the distillation bottom stream of the last distillation column). In another embodiment, the isocyanate condensate obtained, as already described further up, is used for direct (pre) cooling of the liquid phase containing in the collecting zone.

According to the invention, the gaseous phase comprising hydrogen chloride, unconverted phosgene and unliquefied isocyanate and—if present—evaporated solvent which is withdrawn from the collecting zone in step (v) is also worked up (step (viii)).

In this further workup, unliquefied isocyanate in particular is recovered, and solvents (if present in the gas phase withdrawn from the collecting zone in step (v)), excess phosgene and hydrogen chloride gas formed are separated from one another.

The isocyanate recovered is recycled into the process, as elucidated in detail hereinafter. For economic reasons, the solvent (if present in substantial proportions) is preferably also fed back to the process. More particularly, it is preferable to use the recovered solvent as a constituent of the quench liquid, as elucidated in detail further down. For economic reasons, phosgene is preferably likewise fed back to the reaction, especially to step (i). The hydrogen chloride recovered can be sent to various possible uses, for example an oxychlorination of ethylene to ethylene dichloride or a recycling process that affords chlorine, which can be recycled back into the isocyanate process. These recycling processes include the catalytic oxidation of hydrogen chloride, for example by the deacon process, the electrolysis of gaseous hydrogen chloride and the electrolysis of an aqueous solution of hydrogen chloride (hydrochloric acid), obtained by absorption of the hydrogen chloride formed in water.

In step (viii), initially unliquefied isocyanate is recovered from the gaseous phase withdrawn from the collecting zone in step (v).

In one embodiment, this can be done in such a way that the gaseous phase obtained in step (v) comprising (at least) hydrogen chloride, unconverted phosgene and unliquefied isocyanate and—if present—evaporated solvent is firstly partly condensed (i.e. the liquefaction of solvent—if present—and isocyanate is deliberately incomplete) in a step (viii-1) by cooling (i.e. indirect cooling [i.e. without physical contact with a liquid heat transfer medium]; this cooling is preferably conducted in a heat exchanger) to obtain a liquid stream comprising isocyanate and optionally solvent and a gaseous stream comprising hydrogen chloride, phosgene, unliquefied isocyanate and any unliquefied solvent.

In this embodiment, the gaseous stream comprising hydrogen chloride, phosgene, any unliquefied isocyanate and any unliquefied solvent obtained in this way is guided into a scrubbing column for removal of residual isocyanate in step (viii-2) and contacted therein with a scrubbing liquid, giving a liquid stream comprising isocyanate, scrubbing liquid and optionally solvent and a gaseous stream comprising hydrogen chloride and phosgene.

Figure 2A:
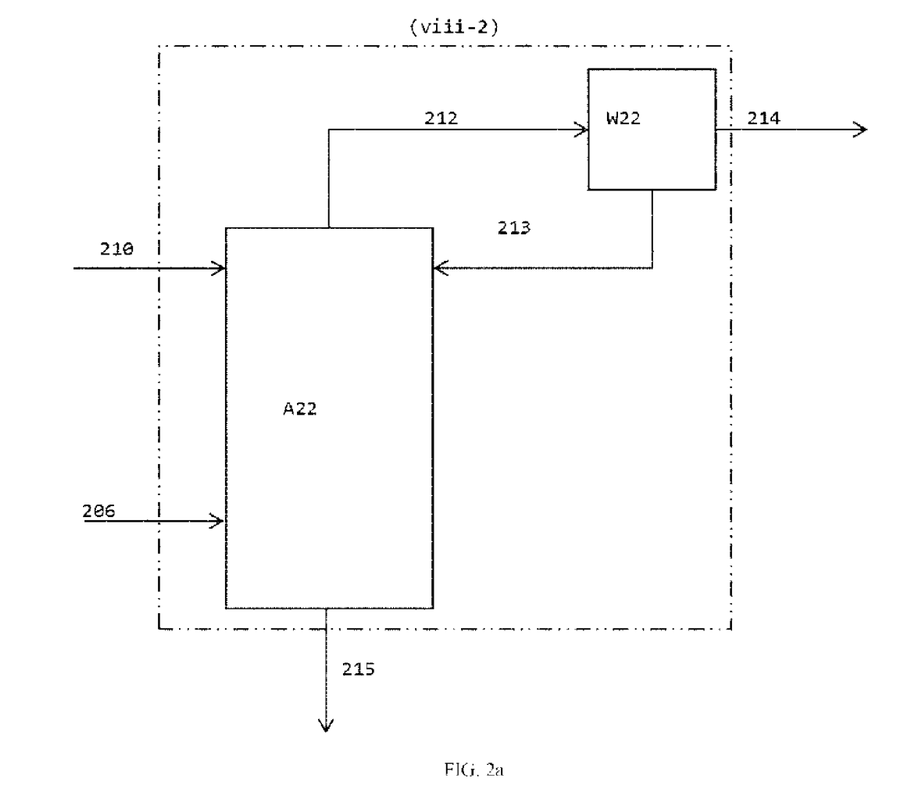
FIG. 2a shows a scrubbing column suitable for being used in all embodiments of the invention, exemplarily illustrated in FIG. 2b.

Suitable scrubbing columns are known to the person skilled in the art. Examples include packed columns and tray columns. There follows a general elucidation of the operation of such a scrubbing column in step (viii-2) with reference to FIG. 2a (FIG. 2a is a detail enlargement of the scrubbing column from FIG. 2b; however, the description that follows is not limited to the embodiment according to FIG. 2b, but is applicable to all embodiments of the invention):

The gaseous material flow (206 in FIG. 2a) that is to be freed of isocyanate by scrubbing is fed to the scrubbing column (A22). The scrubbing liquid required for the purpose is applied at the top of the scrubbing column (A22). The vapors (212) from the scrubbing column pass through a condenser (vapor condenser W22). Of course, it is also possible to use two or more condensers of this kind, especially two, connected in series; it is generally the case that, when the description of the invention refers to "an" apparatus and/or just one apparatus is shown in the drawings, unless stated otherwise, this does not rule out embodiments in which two or more apparatuses are used for the particular purpose. Fractions (213) that are liquefied in the condenser (W22) are returned to the top of and hence recycled into the scrubbing column. The uncondensed fractions (214) containing predominantly hydrogen chloride gas and phosgene, as described further down, are preferably worked up for recovery of hydrogen chloride and phosgene. The greater the isocyanate content in the material flow (206) supplied, the greater the flow rate of scrubbing liquid supplied at the top of the scrubbing column has to be, and the more separation plates are required for reliable retention. The overall scrubbing liquid used in step (viii-2) is composed of the condensate (213) from the condenser (W22) and optionally additionally supplied wash liquid (210). This additionally supplied wash liquid (210) is preferably a solvent stream containing an organic solvent selected from the group consisting of aliphatic hydrocarbons [preferably decahydronaphthalene], aromatic hydrocarbons having no halogen substitution [preferably toluene or xylene, especially toluene], aromatic hydrocarbons having halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents. As will be elucidated in more detail further down, it is possible to dispense with the additionally supplied wash liquid (210) in particular embodiments of the invention.

Figure 2B:
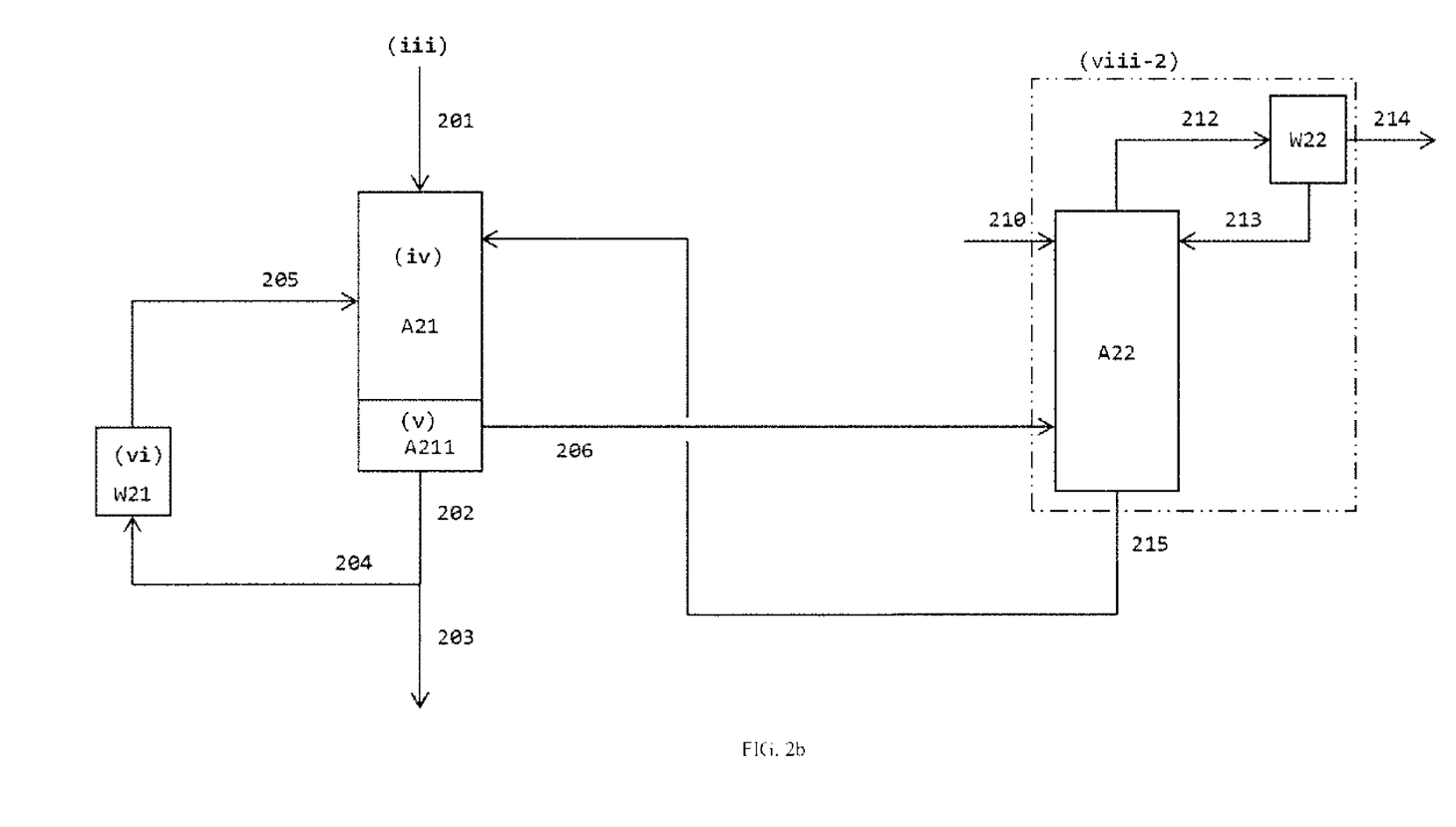
FIG. 2b illustrates a process flow scheme of an embodiment of the invention whereby a gaseous phase (206) comprising hydrogen chloride, unconverted phosgene, unliquefied isocyanate and—if present—evaporated solvent is guided directly into a scrubbing column as shown in FIG. 2a wherein it is contacted with scrubbing liquid to obtain a liquid stream (215) comprising (at least) scrubbing liquid and isocyanate and a gaseous stream (214) comprising hydrogen chloride and phosgene, whereby the liquid stream (215) contains organic solvents only in such proportions that the demands of the invention on the maximum solvent content in the quench liquid used overall in step (iv) are met.

It is possible to guide the gaseous phase comprising hydrogen chloride, unconverted phosgene, unliquefied isocyanate and—if present—evaporated solvent which is obtained in step (v) directly, i.e. without passing through the condensation in step (viii-1), into the scrubbing column from step (viii-2), and to contact it therein with scrubbing liquid to obtain a liquid stream comprising (at least) scrubbing liquid and isocyanate and a gaseous stream comprising hydrogen chloride and phosgene. This is shown in FIG. 2b. By contrast with FIG. 1, all reference numerals begin with the number 2 and otherwise have the same meaning as therein. The apparatus construction corresponds to that shown in FIG. 1. However, the stream (215) obtained in the bottom of the scrubbing column A22—the liquid stream comprising (at least) scrubbing liquid and isocyanate—contains organic solvents only in such proportions that the demands of the invention on the maximum solvent content in the quench liquid used overall in step (iv) are met, by contrast with the bottom stream (115) from the scrubbing column A12 shown in FIG. 1, which, according to the disclosure of application EP 1 935 875 A1, paragraph [0042], contains solvents in proportions of 80% to 99% by mass. In this embodiment, stream 215 serves as an additional quench liquid. The solvent content of stream 215 is adjusted via the choice of composition and flow rate of the scrubbing liquid (210) supplied and via the choice of condensation power of the condenser W22, which is material to the composition and flow rate of the recycle stream of recycled vapor condensate (213). Suitable scrubbing liquid (210) used for the scrubbing column A22 from step (viii-2) is a solvent stream as defined above in the general description of the scrubbing column. It should of course be noted here that the conditions—i.e. especially the flow rates of gas phase to be washed from the collecting zone (step (v); 206), of additionally supplied scrubbing liquid (210) and of recycled vapor condensate (213)—must be chosen such that the demands of the invention with regard to the maximum solvent content of the quench liquid in step (iv) (and of the bottom stream from the scrubbing column) are complied with. It is also possible that the scrubbing liquid (210) supplied additionally contains the isocyanate to be prepared, where the isocyanate used at this point is preferably a portion of the pure isocyanate obtained in step (vii). It is thus possible in principle to dispense largely, especially completely, with the use of solvents as scrubbing liquid (210) additionally supplied to the scrubbing column. In any case, the content of organic solvents in this stream (210) and/or the absolute amount of the stream (210) supplied is chosen such that a proportion of organic solvents of 0.0% by mass to 10% by mass, preferably of 0.0% by masts to 5.0% by mass, based on the total mass thereof, is established in the bottom stream (215) from the scrubbing column (A22). In addition, the bottom stream contains the isocyanate to be prepared.

The process of the invention advantageously enables, rather than using it as quench liquid, guiding of the bottom stream from the scrubbing column into the workup in step (vii), i.e. especially into the distillation for fine purification of the isocyanate in step (vii-2), which is preferably performed in a single distillation column which may especially be configured as a dividing wall column. This is shown—in a general manner—in FIG. 3, where, by contrast with FIG. 1, all reference numerals begin with the number 3 and otherwise have the same meaning as therein. In that case, the quench liquid used in step (iv) is solely the cooled liquid phase of otherwise unchanged composition which is obtained in step (vi). If the fine purification of the isocyanate is preceded upstream by a distillation step (vii-1) for solvent removal—which is not absolutely necessary given the low solvent content in accordance with the invention and is therefore preferably dispensed with—the bottom stream 315 can also be guided into this step (vii-1). The organic solvent, if used, is preferably selected from the group consisting of aliphatic hydrocarbons [preferably decahydronaphthalene], aromatic hydrocarbons having no halogen substitution [preferably toluene or xylene, especially toluene], aromatic hydrocarbons having halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents. Said low solvent content of at most 10% by mass, preferably at most 5.0% by mass, in the bottom stream from the scrubbing column can be achieved by using, as scrubbing liquid additionally supplied to the scrubbing column (stream 310), an organic solvent (preferably without addition of isocyanate) at a flow rate chosen at a correspondingly sufficiently low level. For this purpose, a correspondingly high flow rate of recycled vapor condensate (313) is required. Appropriately, in this embodiment, the scrubbing column (A32) is started up with an initial charge of the same isocyanate which is then circulated via stream 313, such that only an addition of small amounts of fresh solvent via stream (310) is required. In this embodiment, it is also conceivable to entirely dispense with the stream (310) and to use exclusively recycled vapor condensate (313) as scrubbing liquid. In the embodiment according to FIG. 2 as well, it is possible to dispense with the additionally supplied scrubbing liquid (stream 210 therein) when the flow rate of recycled vapor condensate (stream 213 therein) is sufficiently high.

Irrespective of whether or not additional scrubbing liquid (210, 310) is used, and irrespective of whether or not the recycled vapor condensate (213, 313) contains solvents, and irrespective of whether the bottom stream (215, 315) from the scrubbing column (A22, A32) is guided into step (vii) or used as quench liquid, the temperature of the recycled vapor condensate (213, 313) used as scrubbing liquid is preferably adjusted to a temperature of at most 100° C., more preferably of at most 80° C., most preferably of at most 60° C.

Figure 3:
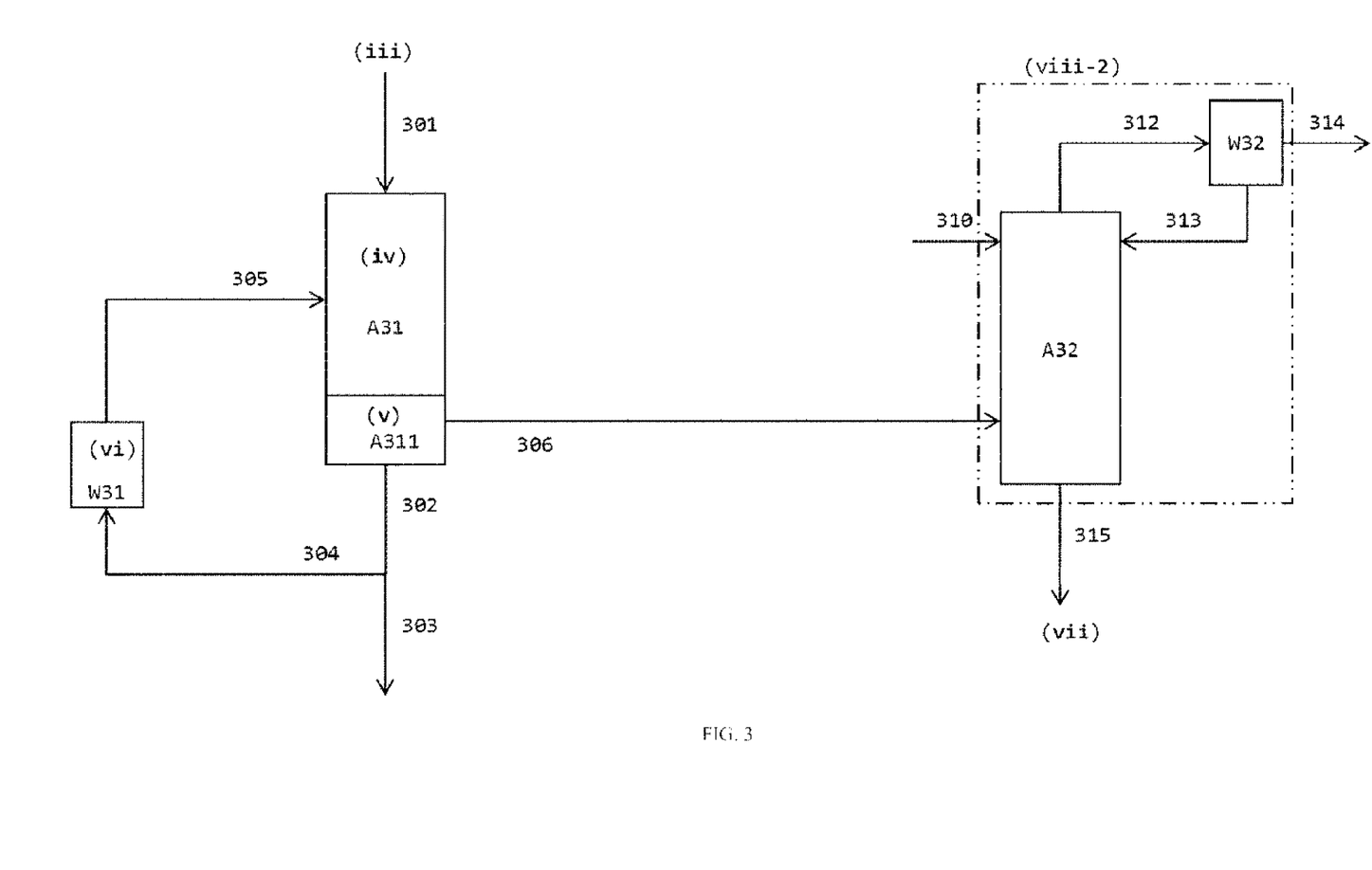
FIG. 3 illustrates a process flow whereby the bottom stream (315) from the scrubbing column (A32) is guided into the workup in step (vii) according to embodiments of the process of the present invention.

In the embodiment of FIG. 3, the gaseous reaction product mixture is cooled in step (iv) solely by recycling of a portion of the liquid phase obtained in step (v) from the collecting vessel. The flow rate of stream 304 and the temperature with which stream 305 is guided into the quench should therefore be chosen so as to assure adequate condensation of the reaction product gas mixture in step (iv). A corresponding design is part of the routine activity of the person skilled in the art.

Owing to the low solvent content of the gas phase withdrawn from the collecting zone in step (v), the process of the invention enables apparatus simplifications of the scrubbing column from step (viii-2). More particularly, it is possible to use a smaller execution of the scrubbing column (preferably with reduced column cross section). Likewise conceivable is a reduction in size of peripheral devices such as condensers.

Irrespective of the exact configuration of step (viii-2), it is preferable to supply the scrubbing column with a minimum amount of fresh organic solvent (by contrast with organic solvent recycled via recycling of the vapor condensate) as scrubbing liquid. In particular, it is preferable to adjust the mass flow rate of fresh organic solvent supplied to the scrubbing column in such a way that it is within the range from 20% to 100%, more preferably within the range from 50% to 100%, of the mass flow rate of the gaseous stream of the primary amine from step (i).

The gaseous stream obtained in step (viii-1) or step (viii-2) is preferably freed of excess phosgene in a step (viii-3) in a manner known per se. This can be effected by means of a cold trap, adsorption in an inert solvent (preferably selected from the group consisting of aliphatic hydrocarbons [preferably decahydronaphthalene], aromatic hydrocarbons having no halogen substitution [preferably toluene or xylene, especially toluene], aromatic hydrocarbons having halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents) or by adsorption and hydrolysis on activated carbon. This step is preferably effected as described in WO2011/003532 A1; see especially page 11 line 31 to page 25 line 15. The gas stream consisting essentially of hydrogen chloride which is obtained in the phosgene removal can be processed further in the manner outlined above.

If organic solvents are used at all in the process of the invention, in all steps in which an organic solvent is used, preference is given to using the same organic solvent which is especially selected from the group consisting of aliphatic hydrocarbons [preferably decahydronaphthalene], aromatic hydrocarbons having no halogen substitution [preferably toluene or xylene, especially toluene], aromatic hydrocarbons having halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents. Particular preference is given to the use of ortho-dichlorobenzene, especially in conjunction with TDA as the primary amine to be phosgenated.

The process of the invention has a series of advantages, especially:
a) reduction of internal solvent circulations;
b) decrease in size or even elimination of solvent distillation in step (vii-1)

c) corresponding saving of evaporation energy to be introduced;
d) reduction in the vapor volumes leaving the collecting zone and hence reduction in size of downstream apparatuses (for example of the isocyanate scrubbing column);
e) higher efficiency of the reactor bottom cooler through maximized heat transfer.

EXAMPLES

Example 1

TDA was evaporated and heated, and hence a stream of 8.8 kg/h of gaseous TDA (380° C., 1600 mbar) was provided (step (i)). In parallel, a stream of 42.8 kg/h of gaseous phosgene (330° C., 1600 mbar) was provided (step (ii)). Mixing, reaction and quenching were conducted in a conical-cylindrical reactor in an upright arrangement that comprised mixing zone, reaction zone, quench zone and collecting zone. For this purpose, the TDA stream was introduced into the reactor from the top by means of a central nozzle tube surrounded by the phosgene stream. At the exit from the central nozzle tube, the amine stream mixed with the enclosing phosgene stream (step (iii)) under adiabatic conditions. The reaction mixture thus obtained flowed downward (still under adiabatic conditions) through the reaction zone (step (iii)) and was cooled down in a quench with a one-stage configuration by injecting quench liquid consisting of recycled reactor bottoms (step (iv)). The mixture of reaction product mixture and quench liquid formed in the quench flowed into the reactor bottoms vessel (the collecting zone; step (v)). According to the invention, 12.1 kg/h of the liquid reactor bottoms that contained 98% by mass of TDI was withdrawn from the collecting zone. 97% of this withdrawn reactor bottoms was cooled down to 150° C. by means of a cooler and injected as the (sole) quench liquid into the quench zone, in a one-stage configuration, of the reactor (step (vi)). The remaining portion of the liquid reactor bottoms withdrawn from the collecting zone was worked up to give TDI (step vii)). After a run time of 92 hours, the metered addition of reactant was stopped and the reactor was cooled down. The assessment of the reactor and cooling zone showed that they were virtually free of solid residues in spite of the largely solvent-free operation.

The process gas leaving the reactor, comprising hydrogen chloride, unconverted phosgene and proportions of unliquefied isocyanate, is suitable for recovery of the isocyanate components in a scrubbing column operated with a low solvent level in the sense of step (viii-2). Owing to the low solvent content, no recycling of the scrubbed-out solvent-containing TDI into the reactor as quench liquid is required.

The yield of the process was 98.2%.

Example 2

The procedure was as described in example 1 except for the following differences:

Flow rate of gaseous TDA (380° C., 1600 mbar): 12000 kg/h

Flow rate of gaseous phosgene (320° C., 1700 mbar): 6000 kg/h

Cooling of the reactor bottoms recycled into the quench: 160° C.

In this example too, the TDI concentration in the TDI raw material was 98% by mass.
The yield of the process was 97.8%.

Example 3 (Comparative Example)

The procedure was as described in example 2 except for the following differences:

The quench zone was in a two-stage configuration, with supply of the upper quench stage with a 10% solution of TDI in ortho-dichlorobenzene and supply of the lower quench stage with the reactor bottoms pumped in circulation, cooled to 160° C. and having a TDI concentration of 35% by mass in ortho-dichlorobenzene.

The yield of the process was 97.6%.

In the inventive examples, it was possible to successfully significantly increase the TDI concentration in the raw material without any associated disadvantages.

The invention claimed is:
1. A process for preparing an isocyanate by phosgenating a corresponding primary amine in the gas phase, comprising:
(i) providing a gaseous stream of a primary amine;
(ii) providing a gaseous phosgene stream;
(iii) mixing the gaseous stream of the primary amine from step (i) and the gaseous phosgene stream from step (ii) to give a gaseous reaction mixture while maintaining a stoichiometric excess of phosgene relative to primary amino groups in a mixing zone and conducting the gaseous reaction mixture thus obtained through a reaction zone for reaction of the primary amine with phosgene to obtain a gaseous reaction product mixture;
(iv) cooling the gaseous reaction product mixture obtained after passage through the reaction zone from step (iii) by contacting the gaseous reaction product mixture with at least one stream of a quench liquid in a quench zone, where the total quench liquid used, based on its total mass, comprises organic solvents in a proportion of at most 25% by mass, where the remainder to 100% by mass comprises the isocyanate to be prepared, to obtain a mixture of reaction product mixture and quench liquid;
(v) conducting the mixture of reaction product mixture and quench liquid obtained in step (iv) into a collecting zone for phase separation, where a liquid phase comprising isocyanate and a gaseous phase comprising hydrogen chloride, unconverted phosgene and unliquefied isocyanate are withdrawn from the collecting zone;
(vi) cooling a portion of the liquid phase comprising isocyanate withdrawn from the collecting zone in step (v), and using the cooled liquid phase as a constituent of the quench liquid;
(vii) working-up the portion of the liquid phase comprising isocyanate withdrawn from the collecting zone in step (v) that has not been cooled down in step (vi), and that has not been used in step (iv) as a constituent of the quench liquid, to obtain the isocyanate;
(viii-1) optionally partly condensing the gaseous phase comprising hydrogen chloride, unconverted phosgene and unliquefied isocyanate which is obtained in step (v) by cooling to obtain a liquid stream comprising isocyanate and a gaseous stream comprising hydrogen chloride, phosgene and unliquefied isocyanate;
(viii-2) guiding either:
when step (viii-1) is conducted, the gaseous stream comprising hydrogen chloride, phosgene and unliquefied isocyanate which is obtained in step (viii-1) or when step (viii-1) is not conducted, the gaseous phase comprising hydrogen chloride, unconverted phosgene and unliquefied isocyanate which is obtained in step (v)

into a scrubbing column in which isocyanate is scrubbed out with a scrubbing liquid to obtain a liquid stream comprising scrubbing liquid and isocyanate and a gaseous stream comprising hydrogen chloride and phosgene, wherein the gaseous stream comprising hydrogen chloride and phosgene obtained thereby is partly condensed in a condenser downstream of the scrubbing column, where the entire scrubbing liquid used in step (viii-2) is composed of the condensate obtained in the condenser downstream of the scrubbing column and optionally additionally supplied scrubbing liquid, where the additionally supplied scrubbing liquid introduces organic solvent into the scrubbing column at most in such an amount that a proportion of organic solvents of 0.0% by mass to 10% by mass is established in the liquid stream comprising scrubbing liquid and isocyanate which is obtained in the scrubbing column, based on the total mass thereof.

2. The process as claimed in claim 1, in which the gaseous reaction product mixture is contacted with the quench liquid in step (iv) by injecting the quench liquid into the gaseous reaction product mixture.

3. The process as claimed in claim 2, in which the contacting of the gaseous reaction product mixture with the quench liquid in step (iv) is effected in one stage.

4. The process as claimed in claim 1, in which the entire scrubbing liquid used in step (viii-2) is composed of the condensate obtained in the condenser downstream of the scrubbing column and additionally supplied scrubbing liquid, where this additionally supplied scrubbing liquid is a solvent stream containing exclusively an organic solvent selected from the group consisting of aliphatic hydrocarbons, aromatic hydrocarbons without halogen substitution, aromatic hydrocarbons with halogen substitution and mixtures of the aforementioned solvents.

5. The process as claimed in claim 4, in which the gaseous stream of primary amine is provided in step (i) simultaneously with additionally supplied scrubbing liquid being supplied to the scrubbing column in step (viii-2), wherein the scrubbing liquid additionally supplied to the scrubbing column in step (viii-2) has a mass flow rate that is 20% to 100% of the mass flow rate of the gaseous stream of primary amine that is provided in step (i).

6. The process as claimed in claim 1, in which the liquid stream comprising scrubbing liquid and isocyanate which is obtained in the scrubbing column is sent to the workup in step (vii).

7. The process as claimed in claim 1, comprising step (viii-1), in which the quench liquid used in step (iv), in addition to the cooled liquid phase obtained in step (vi), comprises the liquid stream comprising isocyanate obtained in step (viii-1).

8. The process as claimed in claim 1, in which the quench liquid used in step (iv), in addition to the cooled liquid phase obtained in step (vi), comprises the liquid stream comprising scrubbing liquid and isocyanate obtained in step (viii-2).

9. The process as claimed in claim 1, in which the quench liquid used in step (iv), aside from the cooled liquid phase obtained in step (vi), does not comprise any further constituents.

10. The process as claimed in claim 1, in which the isocyanate is obtained in step (vii) by supplying the liquid phase comprising isocyanate to a distillative purification without an intermediate solvent column.

11. The process as claimed in claim 10, in which the distillative purification is performed in a single distillation column configured as a dividing wall column.

12. The process as claimed in claim 1, in which every individual stream of quench liquid used in step (iv), based on its total mass, comprises organic solvents in a proportion of at most 25% by mass.

13. The process as claimed in claim 1, in which the primary amine is selected from the group consisting of tolylenediamine, diphenylmethanediamine, xylylenediamine, pentane-1,5-diamine, hexamethylene-1,6-diamine, isophoronediamine, diaminodicyclohexylmethane and mixtures of the aforementioned compounds.

14. The process as claimed in claim 13, in which the primary amine is tolylenediamine.

15. The process as claimed in claim 1, in which, in step (viii-2), organic solvent is introduced into the scrubbing column via the additionally supplied scrubbing liquid at most in such an amount that a proportion of organic solvents of 0.0% by mass to 5.0% by mass is established in the liquid stream comprising scrubbing liquid and isocyanate which is obtained in the scrubbing column, based on the total mass thereof.

* * * * *